US006897462B2

(12) United States Patent
Kawaguchi

(10) Patent No.: US 6,897,462 B2
(45) Date of Patent: May 24, 2005

(54) SURFACE POSITION DETECTION DEVICE AND EXPOSURE APPARATUS AND EXPOSURE METHOD ACHIEVED BY UTILIZING DETECTION DEVICE

(75) Inventor: Toru Kawaguchi, Ageo (JP)

(73) Assignee: Nikon Corporation, Tokyo (JP)

( * ) Notice: Subject to any disclaimer, the term of this patent is extended or adjusted under 35 U.S.C. 154(b) by 371 days.

(21) Appl. No.: 09/832,837

(22) Filed: Apr. 12, 2001

(65) Prior Publication Data
US 2002/0000520 A1 Jan. 3, 2002

(30) Foreign Application Priority Data
Apr. 12, 2000 (JP) .................................. 2000-111314

(51) Int. Cl.$^7$ .............................................. G01N 21/86
(52) U.S. Cl. .................................................. 250/559.22
(58) Field of Search ................................ 356/601–624; 250/559.21–559.27, 559.19, 201.2; 382/103–154; 359/204–218

(56) References Cited

U.S. PATENT DOCUMENTS 5,191,200 A    3/1993    van der Werf et al.
5,602,399 A    2/1997    Mizutani
5,633,721 A    5/1997    Mizutani
6,064,759 A  * 5/2000    Buckley et al. ............. 382/154
6,104,524 A  * 8/2000    Hisano et al. .............. 359/216

FOREIGN PATENT DOCUMENTS

JP    56042205 A     4/1981
JP    7-3995         1/1990
JP    06-097045      4/1994

* cited by examiner

*Primary Examiner*—Tu T. Nguyen
(74) *Attorney, Agent, or Firm*—Finnegan, Henderson, Farabow, Garrett & Dunner, LLP

(57) ABSTRACT

A surface position detection device that detects a surface position of a detection target surface (Wa) includes a projection system (1~6) that projects a light flux onto the detection target surface from a diagonal direction, a light-receiving system (7~14) that receives a light flux reflected from the detection target surface, and a means for light flux deflection (6, 7), which includes an even number of reflection surfaces to allow an incident light flux to exit at an angle not parallel to the incident light flux. The means for light flux deflection is disposed either in the optical path of the projection system or the optical path of the light-receiving system. The surface position of the detection target surface is detected based upon an output from the light-receiving system. Any deterioration in the detection accuracy attributable to outside vibration can be successfully prevented.

33 Claims, 8 Drawing Sheets

SURFACE POSITION DETECTION DEVICE AND EXPOSURE APPARATUS AND EXPOSURE METHOD ACHIEVED BY UTILIZING DETECTION DEVICE

BACKGROUND OF THE INVENTION

The present invention relates to a surface position detection device and an exposure apparatus and an exposure method achieved by utilizing the detection device. More specifically, it relates to detection of the surface position of a photosensitive substrate in a projection exposure apparatus which is employed to transfer a mask pattern onto the photosensitive substrate in the lithography process implemented to manufacture a micro device such as a semiconductor element, a liquid crystal display element, an image-capturing element (such as a CCD) and a thin film magnetic head.

Surface position detection devices ideal in application in projection exposure apparatuses in the known art include the oblique incidence-type surface position detection device disclosed by the applicant of the present invention in Japanese Unexamined Patent Publication No. 42205/1981. In this surface position detection device, detection light is irradiated from a diagonal direction onto a semiconductor wafer set at a position which allows a mask pattern to be transferred onto it through a projection lens. More specifically, a slit pattern is projected onto the detection target surface, i.e., the surface of the semiconductor wafer, by ensuring that the direction along which the long side of the slit pattern extends is perpendicular to the entrance plane (the plane formed of the incident light and the reflected light). Then, by condensing the reflected light, a pattern image is reformed on a detection surface of a means for detection constituted of a photoelectric conversion element and the position at which the pattern image is formed on the detection surface is detected.

In the surface position detection device structured as described above, when the surface of the semiconductor wafer constituting the detection target surface becomes displaced along the vertical direction (displaced along the optical axis of the projection lens), the slit reflection light entering the means for detection becomes shifted laterally along the widthwise direction (the direction along which the short side extends) in correspondence to the vertical displacement. The position of the surface of the semiconductor wafer along the vertical direction is detected based upon the degree of the lateral shift. Thus, based upon the results of the detection, a decision is made as to whether or not the wafer surface is aligned at the focus reference position of the projection lens, i.e., whether or not the wafer surface is aligned on a plane that is conjugate with the surface of the mask pattern projected by the projection lens.

In addition, Japanese Unexamined Patent Publication No. 97045/1994 filed by the applicant of the present invention discloses an improvement on the oblique incidence-type surface position detection device described above, which is capable of performing position detection over a wide area of the detection target surface. This surface position detection device is provided with a projection optical system that projects an image of a specific pattern formed at a first surface onto a wafer surface constituting a detection target surface and a condenser optical system that condenses a light beam having been reflected at the detection target surface and forms an image of the specific pattern on a second surface at, which a light-receiving slit is formed. In addition, Scheimpflug condition is achieved for the first surface and the detection target surface with respect to the projection optical system and Scheimpflug condition is achieved for the detection target surface and the second surface with respect to the condenser optical system.

In this surface position detection device, the projection optical system and the condenser optical system each achieve bilateral telecentricity, to assure that uniform magnification is achieved at the various points on the first surface and the various corresponding points on the detection target surface over the entire surface areas and that uniform magnification is achieved at various points on the detection target surface and various corresponding points on the second surface over, the entire surface areas. By assuming these structural features, a uniform degree of detection accuracy is achieved over the entire detection area on the detection target surface through a detection method based upon the principle of photoelectric microscopy in which the image of the specific pattern formed on the second surface and the light receiving slit are scanned relative to each other to synchronously detect light modulation signals.

SUMMARY OF THE INVENTION

In principle, it is necessary to increase the angle of incidence of a light beam entering the detection target surface (to set the angle of incidence as close as possible to 90°) in order to improve the accuracy with which the surface position of the detection target surface is detected. In such a case, the projection optical system and the condenser optical system will be get close to the detection target surface, creating limits attributable to the proximity of the detection target surface on the structures and the positions of these optical systems. In particular, the components of the optical systems are bound to become large if it is necessary to detect the surface position over a wide range of the detection target surface, resulting in further limits imposed with regard to the structures and the positions. If the working distances of WD of the projection optical system and the condenser optical system are both set large to eliminate such limits on the structures and the positions, larger components are required to constitute the optical systems. Thus, structural and positional limits cannot be effectively eliminated by setting the work distances of optical systems to large values.

The structural and positional restrictions mentioned above may be successfully eliminated by providing a mirror in the optical path of the projection optical system and a mirror in the path of the condenser optical system, which greatly fold the optical path of the incident light beam entering target surface and the optical path of the reflected light beam originating from the detection target surface to allow the projection optical system and the condenser optical system to be set over distances from the detection target surface; as disclosed in Japanese Examined Patent Publication No. 39955/1995 (correspond to Japanese Unexamined Patent Publication No. 6709/1990) filed by the applicant of the present invention (see FIG. 4 in the publication). Alternatively, as disclosed in the same publication (see FIG. 6 in the publication), prisms each having a pair of total internal reflection surfaces which extend parallel to each other may be provided in the optical path of the projection optical system and the optical path of the condenser optical system, to cause parallel displacement of the optical path of the incident light beam entering the detection target surface and the optical path of the reflected light beam originating from the detection target surface and allow the projection optical system and the condenser optical system to be set over distances from the detection target surface.

However, changes are bound to occur in the angles of inclination of the reflection surfaces of the mirrors provided in the optical paths, due to displacement and deformation of the mirror holding members attributable to vibration from the outside, temperature fluctuations and the like. In such a case, a problem occurs in that the angle of incidence and the entry position of the light flux entering the detection target surface and the angle of incidence and the entry position of the light beam entering the detection surface (the second surface) change to result in poor detection accuracy for detecting and the surface position of the detection target surface. On the other hand, when the structure provided with prisms each having a pair of total internal reflection surface of extending parallel to each other is adopted, the detection accuracy is hardly reduced due to vibration from the outside, temperature fluctuations and the like. However, since these prisms retain parallelism between the optical path of the incident light beam and the optical path of the exiting light beam and they do not deflect the light beams at all, the projection optical system and the condenser optical system must distend on both sides radially along the detection target surface and thus, the structural and positional restrictions are not fully eliminated.

SUMMARY OF THE INVENTION

An object of the present invention, which has been completed by addressing the problems of the related art discussed above, is to provide a surface position detection device and method in which deterioration in the detection accuracy attributable to vibration from the outside, temperature fluctuations and the like can be successfully prevented essentially without having to conform to any restrictions imposed by the proximity of the detection target surface on the structures and the positions of the optical systems. Another object of the present invention is to provide an exposure apparatus and an exposure method that achieve highly accurate alignment of a patterned surface of a mask and an exposure target surface of a photosensitive substrate relative to the projection optical system by utilizing the surface position detection device according to the present invention.

In order to achieve the objects described above, in a first aspect of the present invention, a surface position detection device that detects the surface position of a detection target surface comprising a projection system that projects a light flux from a diagonal direction onto the detection target surface and a light-receiving system that receives a light flux having been reflected at the detection target surface, with a means for light flux deflection having an even number of reflection surfaces to cause an incident light flux to be emitted at an angle not parallel to the incident light flux provided, at least, either in the optical path of the projection system or the optical path of the light-receiving system and the surface position of the detection target surface is detected based upon an output from the light-receiving system is provided.

In order to achieve the objects described above, in a first aspect of the present invention, a surface position detection device for detecting a surface position of a detection target surface, comprising: a projection system, optically connected to the detection target surface, for projecting a light beam along an oblique direction onto the detection target surface; a light-receiving system, optically connected to the detection target surface, for receiving a light beam reflected by the detection target surface; a light beam deflector, provided at least either in an optical path of said projection optical system or in an optical path o said light-receiving system, having an even number of reflection surfaces to allow an incident light beam to exit at an angle that is not parallel to the incident light beam, wherein the surface position of the detection target surface is detected based upon an output from the light-receiving system is provided.

In a second aspect of the present invention, a method for detecting a surface position of a detection target, comprising the steps of; projecting a light beam along an oblique direction onto the detection target surface; receiving a light beam reflected by the detection target surface; deflecting at least either one of an optical path of the projected light beam or an optical path of the received light beam with an even number of reflection surfaces to allow an incident light beam to exit at an angle that is not parallel to the incident light beam; and detecting the surface position of the detection target based upon the received light beam, is provided.

In a third aspect of the present invention, an exposure apparatus for exposing a pattern of a mask onto a photosensitive substrate, comprising: the surface position detection device according to the first aspect of the invention, optically connected to said photosensitive substrate; a substrate holder; and a controller, wherein said controller controls a position of the substrate holder based upon an output from said surface position detection device, is provided.

In a fourth aspect of the present invention, a method for exposing a pattern of a mask onto a substrate, comprising the steps of: detecting a position of said substrate with the surface position detective device according to the first aspect of the invention; controlling the position of said substrate based upon an output from said surface position detection device; and exposing the pattern of the mask onto the substrate, is provided.

BRIEF DESCRIPTION OF THE DRAWINGS

The above and other features of the invention and the concomitant advantages will be better understood and appreciated by persons skilled in the field to which the invention pertains in view of the following description given in conjunction with the accompanying drawings which illustrate preferred embodiments.

DETAILED DESCRIPTION OF THE PREFERRED EMBODIMENT

Figure 1:
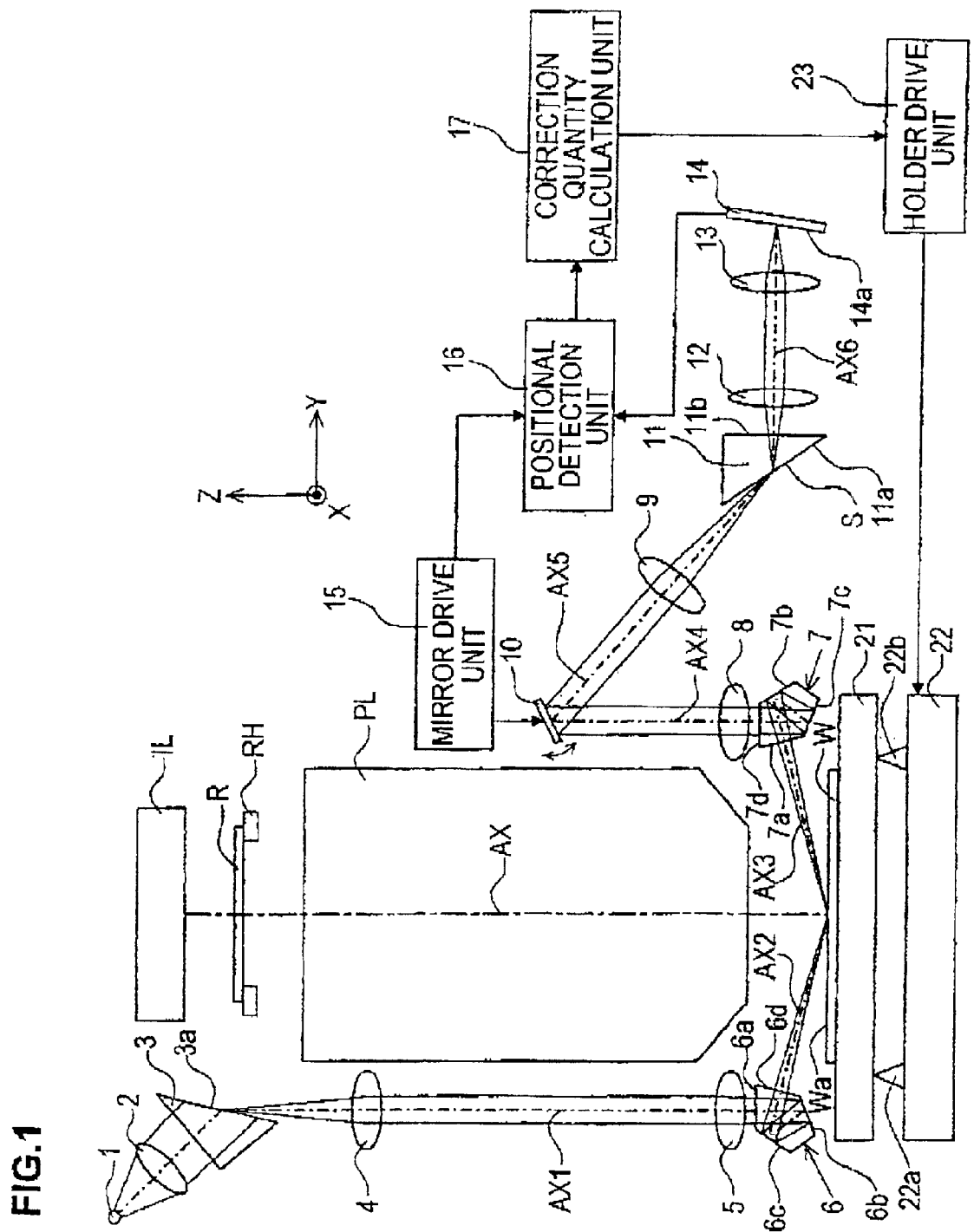
FIG. 1 is a schematic block diagram of a projection exposure apparatus having the surface position detection device in an embodiment of the present invention.

The surface position detection device according to the present invention includes a means for light flux deflection provided either in the optical path of a projection system that projects a light flux onto a detection target surface from a diagonal direction or the optical path of a light-receiving system that receives a light flux having been reflected at the detection target surface and having an even number of reflection surfaces to allow an incident light flux to exit at an angle not parallel to the incident light flux. In a typical implementation mode of the present invention, in which the projection system is provided with a projection optical system that forms a primary image of a specific pattern onto the detection target surface and the light-receiving system is provided with a condenser optical system that forms a secondary image of the specific pattern by condensing a light beam having been reflected at the detection target surface, the light beam deflector is provided both in the optical path between the projection optical system and the detection target surface and in the optical path between the condenser optical system and the detection target surface.

In a more specific example, by forming a reflecting film at a pair of side surfaces of a pentagonal prism facing opposite each other, a light beam deflector is realized in the form of a prism having a pair of reflection surfaces formed therein which are not parallel to each other. In this specification, the pentagonal prism mentioned above is referred to as a pentaprism. An incident light beam entering the pentaprism is directly transmitted through a first transmission surface and is then propagated through the inside of the prism before it is reflected at a first reflection surface. The light beam having been reflected at the first reflection surface and propagated through the inside of the prism is then reflected at a second reflection surface along the optical path intersecting the optical path of the light beam having been transmitted through the first transmission surface. The light beam having been reflected at the second reflection surface and having been propagated through the inside of the prism is allowed to be directly transmitted through a second transmission surface and exit the pentaprism. Thus, the incident light beam having entered the pentaprism provided with a pair of reflection surfaces set to achieve an angle $\Psi$ is deflected by the angle $\Phi$ before it is allowed to exit.

As is to be detailed later, at the pentaprism with its angle of deflection $\Phi$ univocally determined in correspondence to the angle of intersection $\Psi$ of a pair of reflection surfaces, a pair of reflection surfaces are provided by forming a reflecting film at two side surfaces of the pentagonal prism facing opposite each other. Thus, the angle of intersection $\Psi$ formed by the pair of reflection surfaces essentially does not change due to vibration from the outside, temperature fluctuations and the like and, as a result, the angle of deflection $\Phi$ does not change either. Consequently, even when the pentaprism becomes tilted by a slight degree within the plane of incidence (the plane that contains the incident light beam and exiting light beam entering and the exiting the pentaprism) due to displacement and deformation of the holding member attributable to vibration from the outside, temperature fluctuations and the like, the relationship between the angular positions of the pair of reflection surfaces, (i.e., the angle of intersection $\Psi$) remains unchanged, and the angle of deflection $\Phi$ of the prism, too, remains constant. In other words, the direction in which the exiting light beam advances remains unchanged, and the angle of incidence of the light flux entering the detection target surface or the light-receiving surface, too, remains constant. As a result, hardly any change occurs in the angle of incidence and the entry position at the detection target surface or the light-receiving surface, which makes it possible to successfully prevent occurrence of a detection error attributable to vibration from the outside, temperature fluctuations and the like.

In addition, since the optical path of the incident light beam entering the detection target surface and the optical path of the reflected light beam originating from the detection target surface are greatly deflected by the pentaprisms provided in the optical path between the projection optical system and the detection target surface and the optical path between the condenser optical system and the detection target surface according to the present embodiment, the projection optical system and the condenser optical system can be set over distances from the detection target surface to essentially eliminate limits imposed by the proximity of the detection target surface on the structures and the positions of the optical systems.

As described above, the surface position detection device according to the present embodiment successfully prevents any deterioration in the detection accuracy attributable to vibration from the outside, temperature fluctuations and the like, essentially without having to conform to any restrictions imposed by the proximity of the detection target surface on the structures and the positions of the optical systems.

In addition, by utilizing the surface position detection device according to the present embodiment to detect the surface position of the photosensitive substrate relative to a projection optical system in a projection exposure apparatus, highly accurate alignment of the mask pattern surface and the exposure target surface of the photosensitive substrate relative to the projection optical system is achieved, essentially without being affected by vibration of the projection exposure apparatus, the ambient temperature fluctuations ands the like. As a result, it becomes possible to manufacture appropriate micro devices by employing the projection exposure apparatus provided with the surface position detection device according to the presentembodiment.

Embodiments of the present invention are now explained in reference to the attached drawings.

Figure 2:
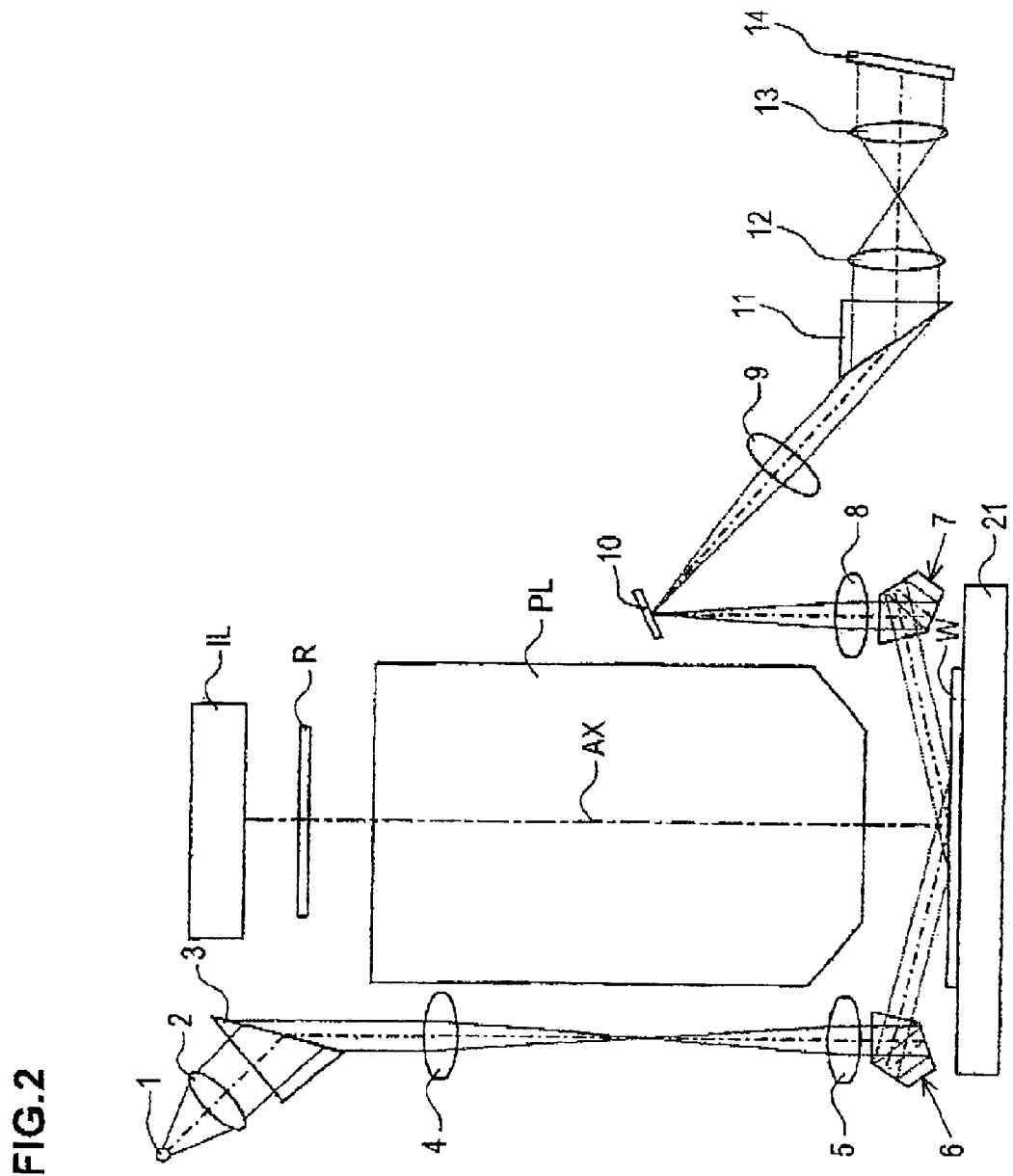
FIG. 2 is an optical path diagram illustrating that the projection optical system and the condenser optical system in FIG. 1 both achieve bilateral telecentricity.

FIG. 1 schematically illustrates the structure of a projection exposure apparatus provided with the surface position detection device in an embodiment of the present invention and FIG. 2 is an optical path diagram illustrating that the projection optical system and the condenser optical system in FIG. 1 both achieve bilateral telecentricity. It is to be noted that in FIG. 1, the Z axis is set parallel to an optical axis AX of a projection optical system PL, the Y axis is set parallel to the surface of the sheet on which FIG. 1 is drawn within a plane perpendicular to the optical axis AX and the X axis is set perpendicular to the surface of the drawing sheet. In this embodiment, the surface position detection device according to the present invention is utilized in a detection of the surface position of a photosensitive substrate in the projection exposure apparatus.

The projection exposure apparatus in the figure is provided with an illumination system IL that evenly illuminates a reticle R constituting a mask at which a specific pattern is formed with illuminating light (exposing light) emitted from an exposing light source (not shown). The reticle R is held parallel to the XY plane on a reticle stage (not shown) via a reticle holder RH. The reticle stage is capable of making two-dimensional movement along the reticle surface (i.e., the XY plane) when driven by a drive system (not shown), and its positional coordinates are measured by a reticle interferometer (not shown) to enable positional control.

Light originating from the pattern formed at the reticle R forms a reticle pattern image on a surface (exposure target surface) Wa of a wafer W as a photosensitive substrate via the projection optical system PL. The wafer W is placed on a wafer holder 21 which, in turn, is supported by a holder supporting mechanism 22. The holder supporting mechanism 22 supports the wafer holder 21 at three support points 22a~22c (FIG. 1 and only shows two support points 22a and 22b) that can move along the vertical direction (direction Z) in conformance to the control implemented by a holder drive unit 23.

Thus, the holder drive unit 23 controls vertical movements of the individual support points 22a~22c of the holder supporting mechanism 22 to allow the wafer holder 21 to be leveled and to move along direction Z (the focusing direction) and ultimately to allow the wafer W to be leveled and to move along direction Z. The wafer holder 21 and the holder supporting mechanism 22 are supported by a wafer stage (not shown). The wafer stage, which is driven by a drive system (not shown), is capable of making two-dimensional movement along the wafer surface (i.e., the XY plane) and rotating around the Z axis, and its positional coordinates are measured by a wafer interferometer (not shown) to enable positional control.

In order to ensure that a circuit pattern provided on the pattern surface of the reticle R is successfully transferred to the individual exposure areas of the exposure target surface Wa of the wafer W, it is necessary to align the current exposure area at the exposure target surface Wa within the width of the depth of focus with respect to the image-forming plane at which at an image is formed through the projection optical system PL for each exposure operation performed to transfer the circuit pattern onto a given exposure area. This alignment may be achieved by first accurately detecting the surface positions of various points in the current exposure area, i.e., the surface positions along the optical axis AX of the projection optical system PL and then leveling and moving the wafer holder 21 along direction Z and, ultimately, leveling and moving the wafer W along direction Z so as to contain the exposure target surface Wa within the range of the width of the depth of focus of the projection optical system PL.

The projection exposure apparatus in the embodiment is accordingly provided with a surface position detection device that detects surface positions at various points in the current exposure area of the exposure target surface Wa. In FIG. 1, the surface position detection device in the embodiment is provided with a light source 1 that supplies detection light. The surface Wa of the wafer typically constituting the detection target surface is covered with a thin film such as a resist. Thus, it is desirable that the light source 1 is a white light source that emits white light having a wide wavelength range, to reduce the degree of the effect of the interference attributable to the thin film. It is to be noted that the light source 1 may be constituted of a light emitting diode or the like that supplies light in a wavelength band that does not manifest a high degree of photosensitivity to the resist.

A divergent light flux from the light source 1 is first converted to an approximately collimated light beam via a condenser lens 2 and then enters a deflecting prism 3. The deflecting prism 3 deflects the approximately collimated light beam from the condenser lens 2 along direction –Z through refraction. In addition, at the exit side of the deflecting prism 3, a transmission-type grating pattern 3a having narrow transmission portions extending along direction X and narrow light blocking portions extending along direction X provided alternately to each other at a constant pitch is formed. It is to be noted that instead of such a transmission-type grating pattern, a reflection-type diffraction grating with indentations and projections may be used or a reflection-type grating pattern having reflection portions and non-reflection portions formed alternately may be utilized.

The light that has been transmitted through the transmission-type grating pattern 3a enters a projection optical system (4, 5) provided along an optical axis AX1 parallel to the optical axis AX of the projection optical system. The projection optical system (4, 5) has constituted of a projection condenser lens 4 and a projection objective lens 5. The light beam having travelled through the projection optical system (4, 5) then enters a pentaprism 6. The pentaprism 6 is a deflecting pentagonal prism with its longer axis running in direction X and is provided with a first transmission surface 6a through which light having entered along the optical axis AM is directly transmitted without becoming refracted. In other words, the first transmission surface 6a is set perpendicular to the optical axis AX1. The light having been transmitted through the first transmission surface 6a and propagated through the inside of the pentaprism 6 along the optical axis AX1 is first reflected at a first reflection surface 6b and then reflected again at a second reflection surface 6c along an optical axis AX2.

The light having been reflected at the second reflection surface 6c and propagated through the inside of the pentaprism 6 along the optical axis AX2 is directly transmitted through a second transmission surface 6d without becoming refracted. In other words, the second transmission surface 6d is set perpendicular to the optical axis AX2. The pentaprism 6 is formed of a low-dispersion and low-thermal-expansion optical material such as quartz glass, and a reflecting film constituted of aluminum, silver or the like is formed both at the first reflection surface 6b and the second reflection surface 6c.

Thus, the light having entered in direction –Z along the optical axis AM is greatly deflected at the pentaprism 6 and reaches the detection target surface Wa at a required angle of incidence along the optical axis AX2. The direction in which the optical axis AX2 extends is set and, therefore, the angle of deflection achieved at the pentaprism 6, too, is set so as to ensure a sufficiently large angle of incidence at the detection target surface Wa at this time. As described above, the pentaprism 6 constitutes a light beam deflector having a pair of reflection surfaces to allow the incident light beam to exit at an angle not parallel to the incident light flux. It is to be noted that a detailed explanation on the structure assumed by the pentaprism 6 and its effects is to be given later.

The device assumes a structure in which the projection optical system (4, 5) sets the surface at which the grating pattern 3a is formed (i.e., the exit surface of the deflecting prism 3) and the detection target surface Wa conjugate with each other when the detection target surface Wa is aligned with the image-forming plane of the projection optical system PL. In addition, the Scheimpflug condition is achieved for the surface at which the grating pattern 3a is formed and the detection target surface Wa with respect to the projection optical system (4, 5). As a result, the light originating from the lattice pattern 3a travels through the projection optical system (4, 5) and forms an image over the entire pattern image-forming plane of the detection target surface Wa with accuracy.

Figure 3:
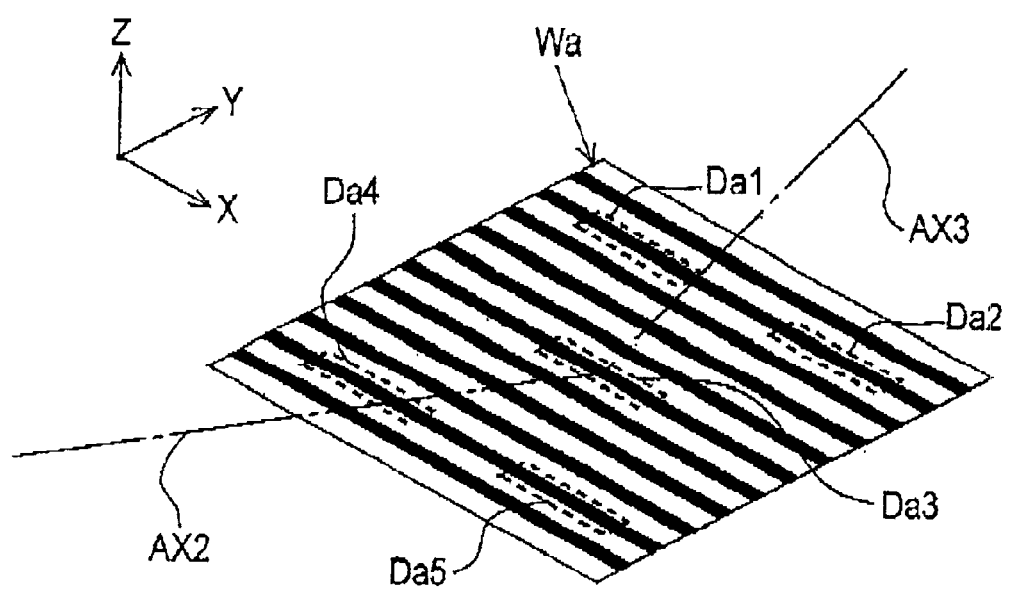
FIG. 3 is a perspective illustrating a primary image of a grating pattern $3a$ formed on the detection target surface Wa.

As indicated by the dotted line representing its optical path in FIG. 2, the projection optical system (4, 5) having the projection condenser lens 4 and the projection objective lens 5 is a so-called bilateral telecentric optical system. Thus, uniform magnification is achieved at various points on the surface at which the grating pattern 3a is formed and at various corresponding points on the detection target surface Wa over the entire surfaces. As shown in FIG. 3, a primary image of the lattice pattern 3a is formed with a high degree of accuracy over the entirety of the detection target surface Wa.

To continue with the explanation in reference to FIG. 1 again, the light having been reflected at the detection target surface Wa enters a condenser optical system (8, 9) via a pentaprism 7 assuming a structure identical to that of the pentaprism 6. Namely, the light having been reflected at the detection target surface Wa enters the pentaprism 7 along an optical axis AX3 symmetrical to the optical axis AX2 relative to the optical axis AX of the projection optical system PL. At the pentaprism 7, light having been transmitted through a first transmission surface 7a perpendicular to the optical axis AX3 is sequentially reflected at a first reflection surface 7b and a second reflection surface 7c and then reaches a second transmission surface 7d along an optical axis AX4 extending along direction Z. Light having been transmitted through the second transmission surface 7d perpendicular to the optical axis AM enters the condenser optical system (8, 9) in direction +Z along the optical axis AX4.

The condenser optical system (8, 9) has a light-receiving objective lens 8 and a light-receiving condenser lens 9. An oscillating mirror 10 constituting a scanning mechanism is provided in the optical path located between the light-receiving objective lens 8 and the light-receiving condenser lens 9. Thus, the light having entered the light-receiving objective lens 8 along the optical axis AM becomes deflected via the oscillating mirror 10 and reaches the light-receiving condenser lens 9 along an optical axis AX5. It is to be noted that while the oscillating mirror 10 is set roughly at the pupil surface of the condenser optical system (8, 9) in this embodiment, the present invention is not restricted by these particulars and the oscillating mirror 10 may be set at any position within the optical path between the detection target surface Wa and the light-receiving surface.

The light having traveled through the condenser optical system (8, 9) then enters a swing and/or tilt correction prism 11 assuming a structure identical to that of the deflecting prism 3. The device assumes a structure in which the condenser optical system (8, 9) sets the detection target surface Wa and an entry surface 11a of the swing and/or tilt correction prism 11 conjugate with each other when the detection target surface Wa is aligned with the image-forming plane of the projection optical system PL. As a result, a secondary image of the lattice pattern 3a is formed at the entry surface 11a of the swing correction prism 11.

Figure 4:
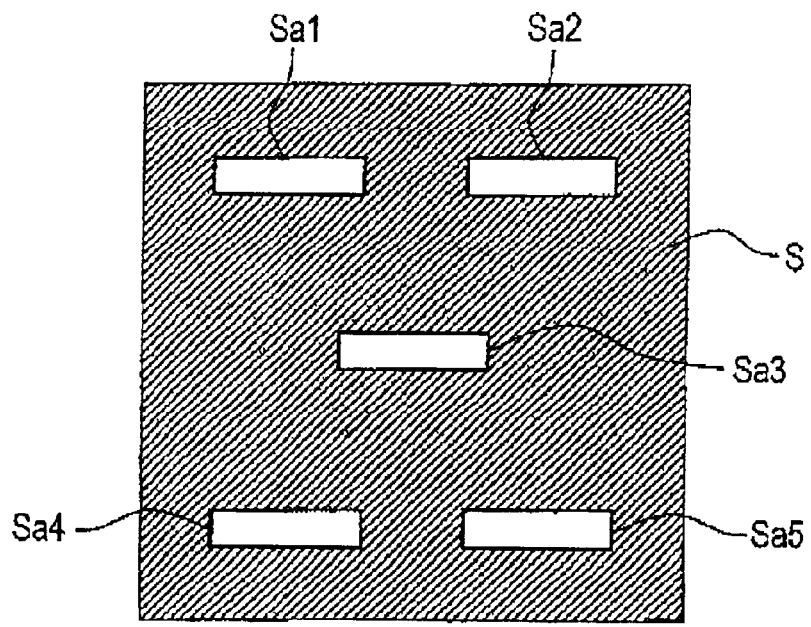
FIG. 4 schematically illustrates the structure of the light-receiving slit S having five rectangular openings Sa1~Sa5 extending along direction X in narrow strips.

It is to be noted that a light-receiving slit S constituting a light blocking member is provided at the entry surface 11a of the swing and/or tilt correction prism 11. As shown in FIG. 4, the light-receiving slit S is provided with a plurality of, e.g., five rectangular openings Sa1~Sa5 extending along direction X in narrow strips. The reflected light from the detection target surface Wa having traveled through the condenser optical system (8, 9) passes through the individual openings Sa1~Sa5 at the light-receiving slit S to enter the swing and/or tilt correction prism 11.

The number of openings Sa at the light-receiving slit S matches the number of detection points on the detection target surface Wa. That is, in FIG. 3 illustrating a primary image of the grating pattern 3a formed the detection target surface Wa, detection points (detection areas) Da1~Da5 on the detection target surface Wa optically correspond to the openings Sa1~Sa5 respectively at the light-receiving slit S in FIG. 4. As a result, the number of detection points on the detection target surface Wa can be increased simply by increasing the number of openings Sa, without complicating the structure of the detection device itself.

It is to be noted that the Scheimpflug condition is achieved for the image-forming plane at which an image is formed by the projection optical system PL and the entry surface 11a of the swing and/or titlt correction prism 11 with respect to the condenser optical system (8, 9). Thus, when the detection target surface Wa is aligned with the image-forming plane, the light originating from the grating pattern 3a travels through the condenser optical system (8, 9) to re-constitute an image with accuracy over the entire pattern image-forming area on the prism entry surface 11a.

In addition, as indicated by the dotted line representing the optical path in FIG. 2, the condenser optical system (8, 9) is a bilateral telecentric optical system. Thus, a uniform magnification is achieved at various points on the detection target surface Wa and the various corresponding points on the prism entry surface 11a. Consequently, a secondary image of the grating pattern 3a is formed with accuracy over the entire entry surface 11a of the swing and/or tilt correction prism 11.

If the light-receiving surface is set at the entry surface 11a of the swing and/or tilt correction prism 11, the angle of incidence of a light beam entering the light-receiving surface increases because of a large angle of incidence θ of the light beam entering the detection target surface Wa. If a silicon photodiode, for instance, is provided at the light-receiving surface under these circumstances, the angle of incidence of the light beam entering the silicon photodiode increases, resulting in a high degree of surface reflection at the silicon photodiode and an eclipse of the light beam which will induce a great reduction in the quantity of light received.

In order to prevent a reduction in the light reception quantity attributable to a large angle of incidence of the light beam entering the light-receiving surface, the entry surface 11a of the swing and/or tilt correction prism 11 constituting the deflection optical system is provided at a plane that is conjugate with the detection target surface Wa relative to the condenser optical system (8, 9) as shown in FIG. 1 in this embodiment. As a result, the light beam having entered the entry surface 11a of the swing and/or tilt correction prism 11 along the optical axis AX5 via the condenser optical system (8, 9) becomes deflected at an angle of refraction which is equal to the apex angle (the angle formed by the entry surface and the exit surface) of the swing and/or tilt correction prism 11 and is emitted from the exit surface 11b along an optical axis AX6. The exit surface 11b is set perpendicular to the optical axis AX6.

Figure 5:
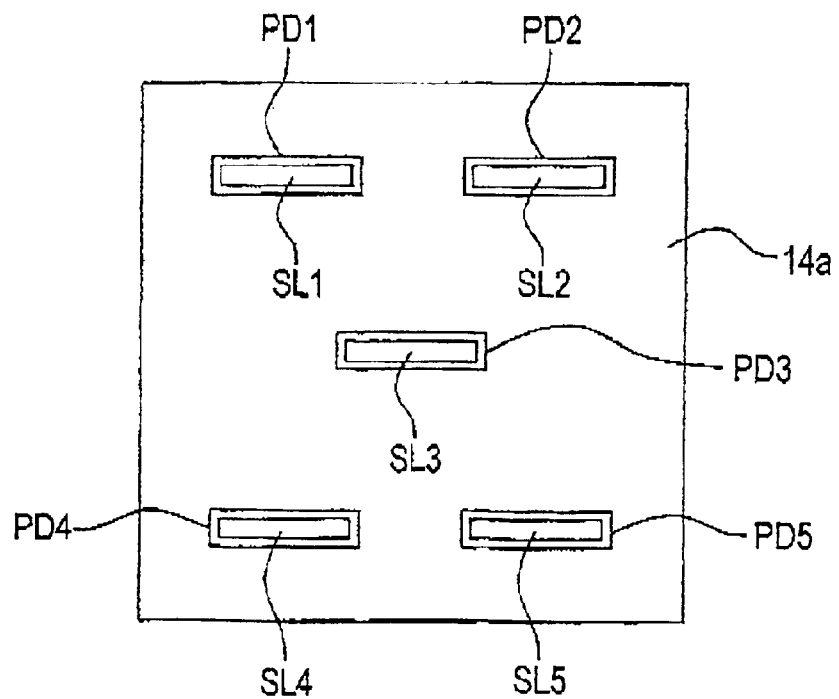
FIG. 5 shows five silicon photodiodes PD1~PD5 provided on the light-receiving surface $14a$ of the light-receiving unit 14 to optically correspond to the openings Sa1~Sa5 of the light-receiving slit S.

The light having been emitted from the exit surface 11b of the swing and/or tilt correction prism 11 along the optical axis AX6 then enters a relay optical system (12, 13) has a pair of lenses 12 and 13. The light having travelled through the relay optical system (12, 13) forms an image which is conjugate with the secondary image of the grating pattern 3a formed on the entry surface 11a of the swing and/or tilt correction prism 11 and the openings Sa1~Sa5 of the light-receiving slit S on the light-receiving surface 14a of a light-receiving unit 14. At the light-receiving surface 14a, five silicon photodiodes PD1~PD5 are provided to optically correspond to the openings Sa1~Sa5 at the light-receiving slit S respectively, as shown in FIG. 5. It is to be noted that instead of silicon photodiodes, a CCD (two-dimensional charge coupled image-capturing element) or photomultiplier may be used.

As described above, in the embodiment in which the swing and/or tilt correction prism 11 is employed as the deflection optical system, the angle of incidence of the light beam entering the light-receiving surface 14a is reduced to a sufficient degree, thereby preventing a reduction in the light reception quantity attributable to a large angle of incidence of the light beam at the light-receiving surface 14a. It is to be noted that it is desirable that the relay optical system (12, 13) be constituted as a bilateral telecentric optical system as illustrated in FIG. 2. In addition, it is desirable that the Scheimpflug condition be achieved for the entry surface 11a of the swing and/or tilt correction prism 11 and the light-receiving surface 14a with respect to the relay optical system (12, 13).

As explained above, the light-receiving slit S having the five openings Sa1~Sa5 is provided on the entry surface 11a of the swing and/or tilt correction prism 11. Thus, the light constituting the secondary image of the grating pattern 3a formed on the entry surface 11a is partially blocked via the light-receiving slit S. That is, only the light beam from the secondary image of the grating pattern 3a formed over the area corresponding to the openings Sa1~Sa5 at the light-receiving slit S is allowed to reach the light-receiving surface 14a via the swing and/or tilt correction prism 11 and the relay optical system (12, 13).

Thus, as shown in FIG. 5, images of the openings Sa1~Sa5 at the light-receiving slit S, i.e., slit images SL1~SL5, are respectively formed on the silicon photodiodes PD1~PD5 provided on the light-receiving surface 14a of the light-receiving unit 14. It is ensured that the slit images SL1~SL5 are formed inside the rectangular light-receiving areas of the silicon photodiodes PD1~PD5.

When the detection target surface Wa moves vertically in direction Z along the optical axis AX of the projection optical system PL, the secondary image of the grating pattern 3a formed on the entry surface 11a of the swing and/or tilt correction prism 11 becomes laterally shifted along the direction of the pattern pitch in response to the vertical movement of the detection target surface Wa. In the embodiment, the extent of the lateral shift occurring in the secondary images of the grating pattern 3a is detected and the surface position of the detection target surface Wa along the optical axis AX of the projection optical system PL is detected in correspondence to the detected lateral shift quantity, based upon, for instance, the principle of photoelectric microscopy disclosed in Japanese Unexamined Patent Publication No. 42205/1981. The following is a brief explanation of a surface position detection achieved based upon the principle of photoelectric microscopy.

As described earlier, FIG. 1 shows the oscillating mirror 10 provided within the optical path of the condenser optical system (8, 9), which is driven to rotate forward/backward around the X axis by a mirror drive unit 15. The mirror drive unit 15 oscillates the oscillating mirror 10 over a specific cycle T along the direction indicated by the arrow in the figure, in response to a signal provided by an internal oscillator. As the oscillating mirror 10 oscillates, the secondary image of the grating pattern 3a formed on the entry surface 11a of the swing and/or tilt correction prism 11, too, oscillate along the direction of the pattern pitch. At this time, the oscillation of the secondary image of the grating pattern 3a causes a change in the quantities of light transmitted through the openings Sa1~Sa5 at the light-receiving slit S. The light transmitted through the light-receiving slit S travels through the relay optical system (12, 13) and reaches the silicon photodiodes PD1~PD5 provided on the light-receiving surface 14a of the light-receiving unit 14.

The explanation is simplified by focusing on the light reaching one of the silicon photodiodes, i.e., the silicon photodiode PD1. The light having been transmitted through the opening Sa1 at the light-receiving slit S forms the slit image SL1 on the silicon photodiode PD1. The brightness of the slit image SL1 changes as the oscillating mirror 10 oscillates. In the embodiment, the width of the opening Sa1 (i.e., the measurement of the secondary image of the grating pattern 3a along the direction of the pitch) is set equal to or smaller than ½ of the pitch of the secondary image of the grating pattern 3a and, thus, the amplitude of the secondary image of the grating pattern 3a is set equal to or smaller than ½ the pitch.

In addition, it is ensured that the center of the opening Sa1 is aligned with the center of the oscillation of the secondary image of the grating pattern 3a when the detection target surface Wa is aligned with the image-forming plane of the projection optical system PL. Thus, when the secondary image of the grating pattern 3a oscillates as a result of the oscillation of the oscillating mirror 10, the light reception quantity at the silicon photodiode PD1 changes. The silicon photodiode PD1 at the light-receiving unit 14 outputs a detection signal corresponding to the change in the light intensity of the slit image SL1, i.e., a detection signal reflecting the light modulation occurring in the slit image SL1, to a positional detection unit 16. Likewise, the silicon photodiodes PD2~PD5, too, output detection signals corresponding to the light modulation occurring in the slit images SL1~SL5 to the positional detection unit 16.

In addition, the mirror drive unit 15 also provides an AC signal at a phase matching that of the oscillation cycle T of the oscillating mirror 10 to the positional detection unit 16. The positional detection unit 16 performs synchronous rectification, i.e., synchronous phase detection of the detection signals provided by the silicon photodiodes PD1~PD5 at the light-receiving unit 14 in reference to the phase of the AC signal at the cycle T and outputs the resulting phase detection output signals to a correction quantity calculation unit 17. The phase detection output signals output from the positional detection unit 16 are normally referred to as S curve signals each set to 0 level when the corresponding detection area among the detection areas Da1~Da5 on the detection target surface Wa is set on the image-forming plane of the projection optical system PL, i.e., when the detection signal is undergoing a change, with a cycle which is ½ the oscillation cycle T of the oscillating mirror 10.

The phase detection output signals indicate a positive level when the corresponding detection areas Da1~Da5 at the detection target surface Wa are displaced further upward relative to the imageforming plane of the projection optical system PL, whereas they indicate a negative level when the detection areas Da1~Da5 at the detection target surface Wa are displaced further downward relative to the image-forming plane of the projection optical system PL. In other words, the phase detection output signals each indicate an output value corresponding to the change in the surface position of the detection target surface Wa. The correction quantity calculation unit 17 calculates the individual positions of the detection areas Da1~Da5 on the detection target surface Wa along direction Z based upon the positive/negative levels of the phase detection output signals that have been provided to determine the average inclination of the detection target surface Wa and its position along direction Z.

Then, the correction quantity calculation unit 17 calculates a tilt correction quantity and a direction Z correction quantity required to contain the detection target surface Wa within the range of the depth of focus of the projection optical system PL, and provides the correction quantities thus calculated to the holder drive unit 23. The holder drive unit 23 implements drive control the holder supporting mechanism 22 based upon the tilt correction quantity and the direction Z correction quantity to level the wafer holder 21 and also move it along direction Z, and ultimately to level the wafer W and move the wafer W along direction Z. The wafer W is, as a result, aligned relative to the projection optical system PL with a high degree of accuracy so as to contain the current exposure area at the exposure target surface Wa within the range of the depth of focus of the projection optical system PL. It is to be noted that specific details of the Scheimpflung condition, the structures and effects of the deflecting prism 3 and the swing and/or tilt correction prism 11 and the application of the principle of photoelectric microscopy are disclosed in Japanese Unexamined Patent Publication No. 97045/1994 filed by the applicant of the present invention.

Next, a detailed explanation is given on the structures assumed by and the effects achieved by the pentaprisms 6 and 7 constituting the light beam deflector. As explained above, since the pentaprisms 6 and 7 adopt structures identical to each other, they achieve similar advantages. The following explanation focuses on the structure and the advantages of the pentaprism 6, for purposes of simplification. The pentaprism 6 in FIG. I greatly deflects a light beam traveling from above along direction −Z, so that deflected light advances along an almost horizontal direction to enter the detection target surface Wa at a desired, relatively large angle of incidence.

Figure 6:
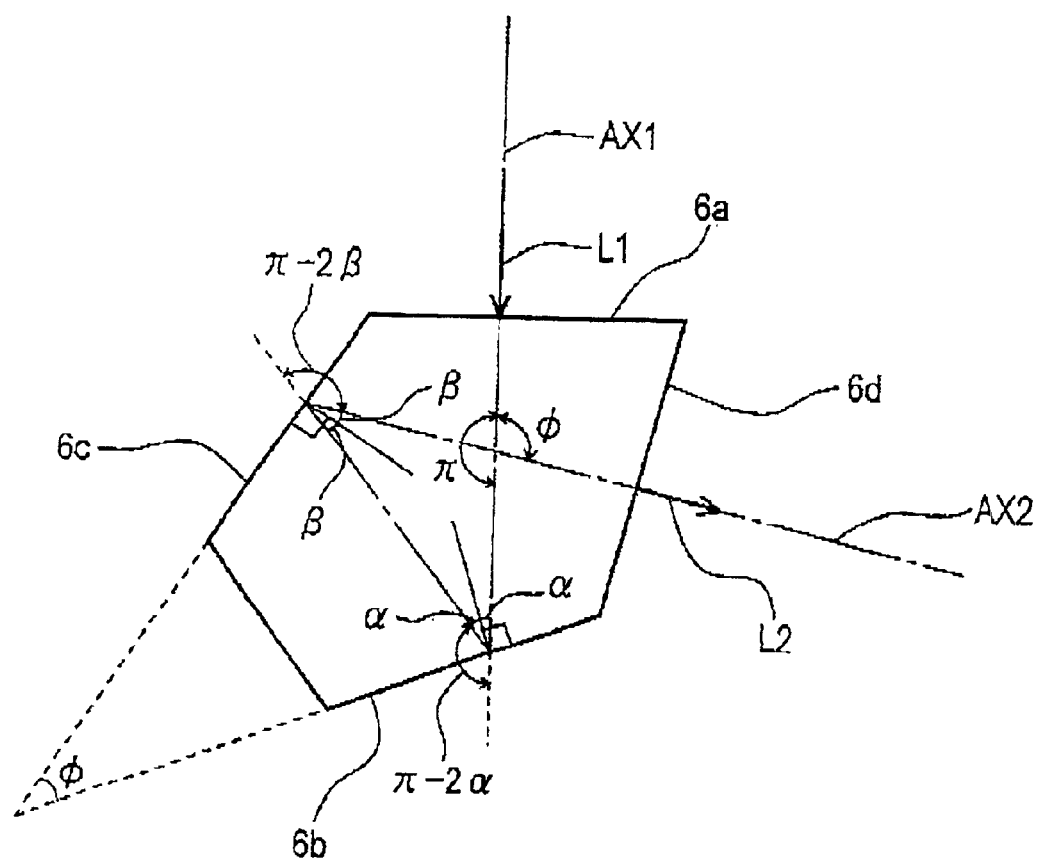
FIG. 6 shows the relationship between the angle of intersection formed by the pair of reflection surfaces at the pentaprism 6 in FIG. 1 and the angle of deflection.

FIG. 6 illustrates the relationship between the angle of intersection formed by the pair of reflection surfaces at the pentaprism 6 in FIG. 1 and the angle of deflection achieved at the pentaprism 6. In FIG. 6, a light ray L 1 having entered the pentaprism 6 along the optical axis AX1 is sequentially reflected at the first reflection surface 6b and the second reflection surface 6c and then is emitted from the pentaprism 6 as a light ray L2 traveling along the optical axis AX2. In other words, the pentaprism 6 deflects the incident light ray L 1 by an angle ($\phi$). The relationship as expressed in the following equation (1) is achieved between the angle of intersection $\Psi$ formed by the first reflection surface 6b and the second reflection surface 6c and the angle of deflection ($\phi$) formed by the incident light ray L 1 and the exiting light ray L 2.

$$\phi+\pi=(\pi-2\alpha)+(\pi-2\beta) \quad (1)$$

In the equation above, $\alpha$ represents the angle of incidence at which the light ray having entered the pentaprism 6 along the optical axis AX1 enters the first reflection surface 6b and $\beta$ represents the angle of incidence at which the light ray having entered the pentaprism 6 along the optical axis AX1 enters the second reflection surface 6c. These angles of incidence $\alpha$ and $\beta$ achieve a relationship to the angle of intersection $\Psi$ as expressed in the following equation (2).

$$\Psi=\alpha+\beta \quad (2)$$

Thus, equation (1) can be modified as expressed in the following equation (3).

$$\phi+\pi=2\pi-2(\alpha+\beta)=2\pi-2\phi \quad (3)$$

Based upon equation (3), the angle of deflection $\phi$ is expressed as in the following equation (4).

$$\phi=\pi-2\Psi \quad (4)$$

Equation (4) indicates that the sole determining factor of the angle of deflection ($\phi$) of the pentaprism 6 is the angle of intersection $\Psi$ formed by the pair of reflection surfaces 6b and 6c, i.e., the angle of deflection $\phi$ is univocally determined by the angle of the intersection $\Psi$. As described above, the pair of reflection surfaces 6b and 6c are constituted by forming a reflecting film on two side surfaces facing opposite each other at the pentagonal prism formed as an integrated unit by using quartz gloss. As a result, the angle of intersection $\Psi$ formed by the pair of reflection surfaces essentially does not change and ultimately, the angle of deflection ($\phi$) of the pentaprism 6 does not change either, due to vibration from the outside, temperature fluctuations and the like.

Since the relationship between the angular positions (i.e., the angle of intersection $\Psi$) between the pair of reflection surfaces 6b and 6c is kept even when the pentaprism 6 rotates by a slight degree around, for instance, the X axis (within the plane of incidence containing the optical axes AX1 and AX2) due to displacement or deformation of the holding member attributable to vibration from the outside, temperature fluctuations and the like in this embodiment, the angle of deflection ($\phi$) of the pentaprism 6, too, remains constant, i.e., the direction along which the exiting light ray L 2 travels remains unchanged and, thus, the angle of incidence of the light beam entering the detection target surface Wa does not change either. While the spatial position of the exiting light ray changes in correspondence to the distance between the pair of reflection surfaces 6b and 6c, i.e., the exiting light ray L 2 in FIG. 6 undergoes a lateral shift parallel to the optical axis AX2, the degree of this lateral shift is insignificant enough to be disregarded in practical application, which means that the degree of positional shift occurring with regard to the light beam entering the detection target surface Wa as a result of the lateral shift, too, is slight enough to be disregarded in practical application.

In contrast, if a conventional reflecting mirror (a mirror having a single reflection surface) is provided in place of the pentaprism 6 as in the prior art, a slight rotation of the reflection surface of the reflecting mirror around, for instance, the X axis, caused by displacement or deformation of the holding member attributable to vibration from the outside, temperature fluctuations and the like will result in the angle of deflection of the reflecting mirror changing by twice the tilt angle (the angle of the slight rotation) and, consequently, the position at which the light beam enters the detection target surface changes together with the angle of incidence at the detection target surface. Under these circumstances, the degree by which the entry position changes is almost in proportion to the change in the angle of incidence and the distance between the detection target surface and the reflection surface of the reflecting mirror.

The change in the angle of incidence occurring at this time relates to a change in the detection conversion coefficient used when detecting the surface position of the detection target surface and the change in the entry position results in a change in the position at which the pattern image is formed, and thus, either of these changes induces a detection error in detecting the position of the detection target surface. In other words, even when the surface position of the detection target surface does not change at all in reality, the position at which the pattern image is formed on the light-receiving slit changes as a result of a change in the angle of incidence or a change in the entry position attributable to the change in the angle of deflection of the reflecting mirror. As a result, an erroneous detection is performed to indicate that a change has occurred in the surface position of the detection target surface which actually has not changed.

As explained above, even when the pentaprism, 6 becomes tilted by a slight degree within the plane of incidence as a result of displacement or deformation of the holding member attributable to external vibration, temperature fluctuations and the like, the angle of deflection of the pentaprism 6 remains constant and, therefore, the angle of incidence at the detection target surface remains unchanged in the embodiment. Thus, unlike in the prior art in which a reflecting mirror that reflects light at a single surface is employed, a detection error attributable to external vibration, temperature fluctuations and the like can be successfully eliminated by preventing a change in the angle of incidence and a change in the entry position which is affected by the distance between the detection target surface and the reflecting mirror.

Similar advantages are achieved at the pentaprism 7 to those achieved at the pentaprism 6. That is, even when the pentaprism 7 becomes tilted by a slight degree within the plane of incidence as a result of displacement or deformation of the holding member attributable to vibration from the outside, temperature fluctuations and the like, the angle of deflection of the pentaprism 7 does not change and therefore, the angle of incidence at the light-receiving slit S and the angle of incidence at the light-receiving surface 14a do not change either. Thus, unlike the prior art in which a reflecting mirror that reflects light at a single surface is employed, a detection error attributable to vibration from the outside, temperature fluctuations and the like can be successfully eliminated by preventing a change in the angle of incidence at the light-receiving slit S and a change in the entry position which is affected by the distance between the reflecting mirror and the light-receiving slit S.

In addition, in the embodiment, the pentaprisms 6 and 7 are respectively provided in the optical path between the projection optical system (4, 5) and the detection target surface Wa and the optical path between the condenser optical system (8 , 9) and the detection target surface Wa to greatly deflect the optical path of the light beam entering the detection target surface Wa and the optical path of a light beam having been reflected at the detection target surface Wa through the pentaprisms 6 and 7, so as to allow the projection optical system (4, 5) and the condenser optical system (8, 9) to be set over sufficient distances from the detection target surface Wa. As a result, the structures and the positions of the projection optical system (4, 5) and the condenser optical system (8, 9) are essentially free of any limits that may otherwise be imposed by the proximity of the detection target surface Wa.

As described above, the surface position detection device in the embodiment, which essentially remains free of any limits imposed by the proximity of the detection target surface Wa with regard to the structures and the positions of the optical systems successfully prevents deterioration in the detection accuracy attributable to vibration from the outside, temperature fluctuations and the like. As a result, a projection exposure apparatus provided with the surface position detection device in the embodiment, which remains essentially unaffected by vibration of the apparatus, ambient air temperature fluctuations and the like, is capable of achieving highly accurate alignment of the mask pattern surface and the exposure target surface of the photosensitive substrate relative to the projection optical system and, thus, is capable of manufacturing appropriate micro devices.

However since deflected light beams are shifted slightly (the positions at which light beams exit the pentaprisms change) as a result of slight inclinations of the pentaprisms 6 and 7 in this embodiment, it is desirable to form the pentaprisms in a size which is small as possible (to minimize the lengths of the optical paths within the pentaprisms). Since the required angle of intersection $\Psi$ of the pair of reflection surfaces is defined in conformance to the required angle of deflection ($\phi$) through equation (4) explained earlier, each pentaprism is formed in a compact size in correspondence to the required angle of intersection $\Psi$ and the pair of effective reflection areas that should be assured.

It is to be noted that if the angle of intersection of the pair of reflection surfaces is changed due to thermal expansion of the pentaprism itself, the angle of deflection (and ultimately, the angles of incidence and the entry positions at the detection target surface and the light-receiving surface) changes to induce a detection error. Accordingly, it is desirable to constitute the pentaprism with an optical material that does not readily expand when heated such as quartz glass. More specifically, it is desirable to constitute the pentaprism with an optical material having a coefficient of thermal expansion equal to or lower than 1 ppm/K, and the coefficient of thermal expansion of quartz glass is approximately 0.5 ppm/K satisfying this requirement.

Examples of such low thermal expansion glass materials include titanium silicate glass (e.g., ULE (trademark) available from Corning Incorporated in New York State, USA), Zerodur (trademark) available fromSchotts Glas in Mainz, Germany, Cliarceram-Z (trademark) available from Ohara Corp. in Sagamihara, Kanagawa Prefecture and the like. The coefficient of thermal expansion achieved by ULE is +0.05 ppm/K, the coefficient of thermal expansion achieved by Zerodur is −0.03 ppm/K and the coefficient of thermal expansion achieved by Cliarceram-Z is 0.08 ppm/K. It is to be noted that quartz glass is the most desirable low thermal expansion glass material since it achieves an optimal transmittance.

In addition, it is desirable to form the pentaprisms with a low-dispersion optical material such as quartz glass in order to reduce the occurrence of chromatic aberration inside the prisms. In more specific terms, the optical material used to constitute the pentaprisms should have an Abbe number of 65 or higher and quartz glass has an Abbe number of approximately 68, satisfying the requirement.

As mentionedabove, the angle of incidence at which the light beam enters the detection target surface Wa should be set as large as possible (set as close to 90'as possible) to improve the accuracy with which the surface position of the detection target surface Wa is detected. Since the light beam entering along direction −Z is deflected by the deflection angle $\Psi$ to allow it to enter the detection target surface Wa parallel to the XY plane in the embodiment, the relationship expressed as $\phi=\pi-\theta$ is achieved between the angle of incidence $\theta$ and the angle of reflection $\theta$ at the detection target surface Wa and the angle of deflection $\theta$.

When the desired angle of incidence $\theta$ and angle of reflection $\theta$ are set at, for instance, $80°\leq\theta<90°$ angle of deflection $\theta$ at the pentaprism is within a range of $100°\geq\theta>90°$, which it sets the angle of intersection $\Psi$ of the pair of reflection surfaces at the pentaprism within a range of $40°\leq\Psi<45°$ in conformance to the relationship expressed in equation (4). In other words, by using a pentaprism achieving an angle of intersection $\Psi$ within a range of $40°\geq y>45°$, the angle of incidence of the light beam entering the detection target surface Wa can be set at a desirable value, and then the projection optical system (4, 5) and the condenser optical system (8, 9) can be positioned along the vertical direction as is the projection optical system PL.

Figure 7:
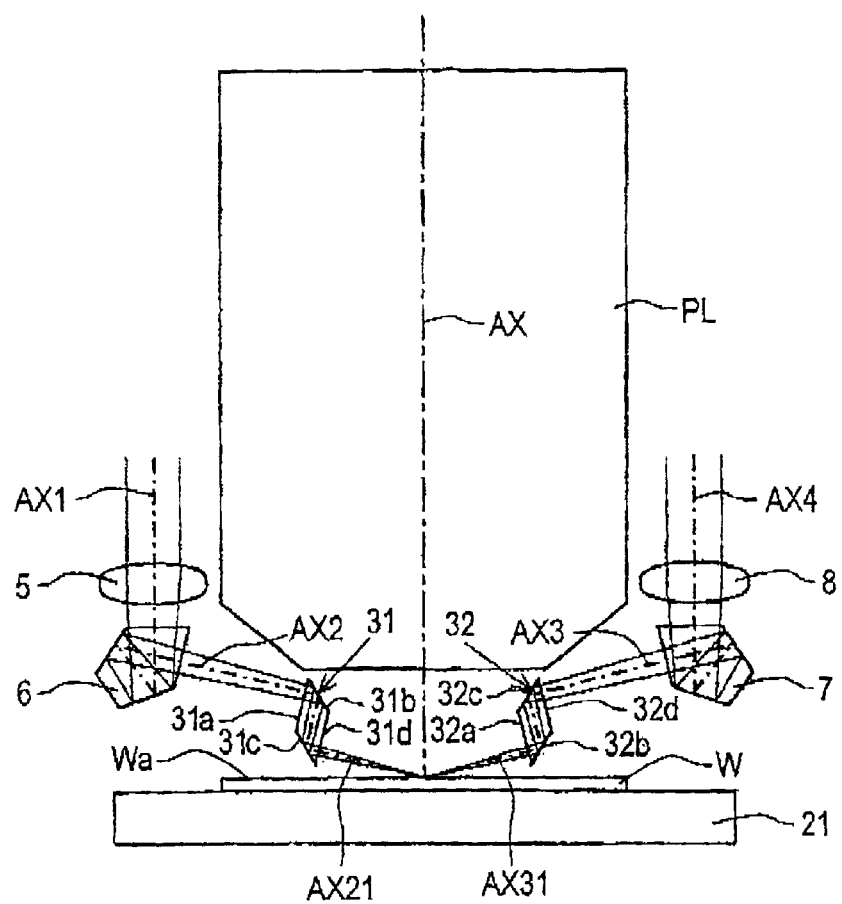
FIG. 7 schematically illustrates the structure of an essential portion of a projection exposure apparatus having a surface position detection device achieved as a variation of the first embodiment.

FIG. 7 schematically illustrates the structure of an essential portion of a projection exposure apparatus provided with a surface position detection device achieved as a variation of the embodiment shown in FIG. 1. The variation in FIG. 7 assumes a structure similar to that adopted in the embodiment shown in FIG. 1. However, the variation in FIG. 7 differs from the embodiment shown in FIG. 1 in that rhombic prisms 31 and 32 are respectively provided in the optical path between the pentaprism 6 and the detection target surface Wa and the optical path between the pentaprism 7 and the detection target surface Wa. The same reference numbers as those in FIG. 1 are accordingly assigned elements achieving functions identical to the components in the embodiment shown in FIG. 1. The following is an explanation of the variation shown in FIG. 7 by focusing on the differences from the embodiment in FIG. 1.

In the variation in FIG. 7, a light beam having exited the pentaprism 6 along the optical axis AX2 enters the rhombic prism 3 1. The rhombic prism 31 is a quadrangular prism having a rhombic cross section and its longer axis extends along direction X as does the longer axis of the pentaprism 6. At the rhombic prism 31, light having been transmitted through a first transmission surface 31a perpendicular to the optical axis AX2 is sequentially reflected at a pair of reflection surfaces 31b and 31c which are parallel to each other, is then transmitted through a second transmission surface 31d parallel to the first transmission surface 31a and exits the rhombic prism 31 along an optical axis AX21 parallel to the optical axis AX2. The light beam having exited the rhombic prism 31 along the optical axis AX21 then enters the detection target surface Wa.

A light beam having been reflected at the detection target surface Wa along an optical axis AX31 that is symmetrical to the optical axis AX21 relative to the optical axis AX of the projection optical system PL, on the other hand, enters the rhombic prism 32. The rhombic prism 32, which is similar to the rhombic prism 31, is a quadrangular prism having its longer axis extending along direction X and having a rhombic cross section. As a result, at the rhombic prism 32, light having been transmitted through a first transmission surface 32a perpendicular to the optical axis AX31 is sequentially reflected at a pair of reflection surfaces 32b and 32c parallel to each other, is transmitted through a second transmission surface 32d parallel to the first transmission surface 32a and exits the rhombic prism 32 along an optical axis AX3 parallel to the optical axis AX3 1.

As explained above, in the variation shown in FIG. 7, which is provided with the rhombic prisms 31 and 32 respectively in the optical path between the pentaprism 6 and the detection target surface Wa and the optical path between the pentaprisin 7 and the detection target surface Wa, the optical path of the light beam entering the detection target surface Wa and the optical path of the light beam having been reflected at the detection target surface Wa are caused to undergo parallel movement by the rhombic prisms 31 and 32 respectively. As a result, the pair of optical prisms 6 and 7 can be set over distances from the detection target surface Wa to essentially free the pair of pentaprisms and their holding members from any structural and positional restrictions imposed by the proximity of the detection target surface Wa.

Figure 8:
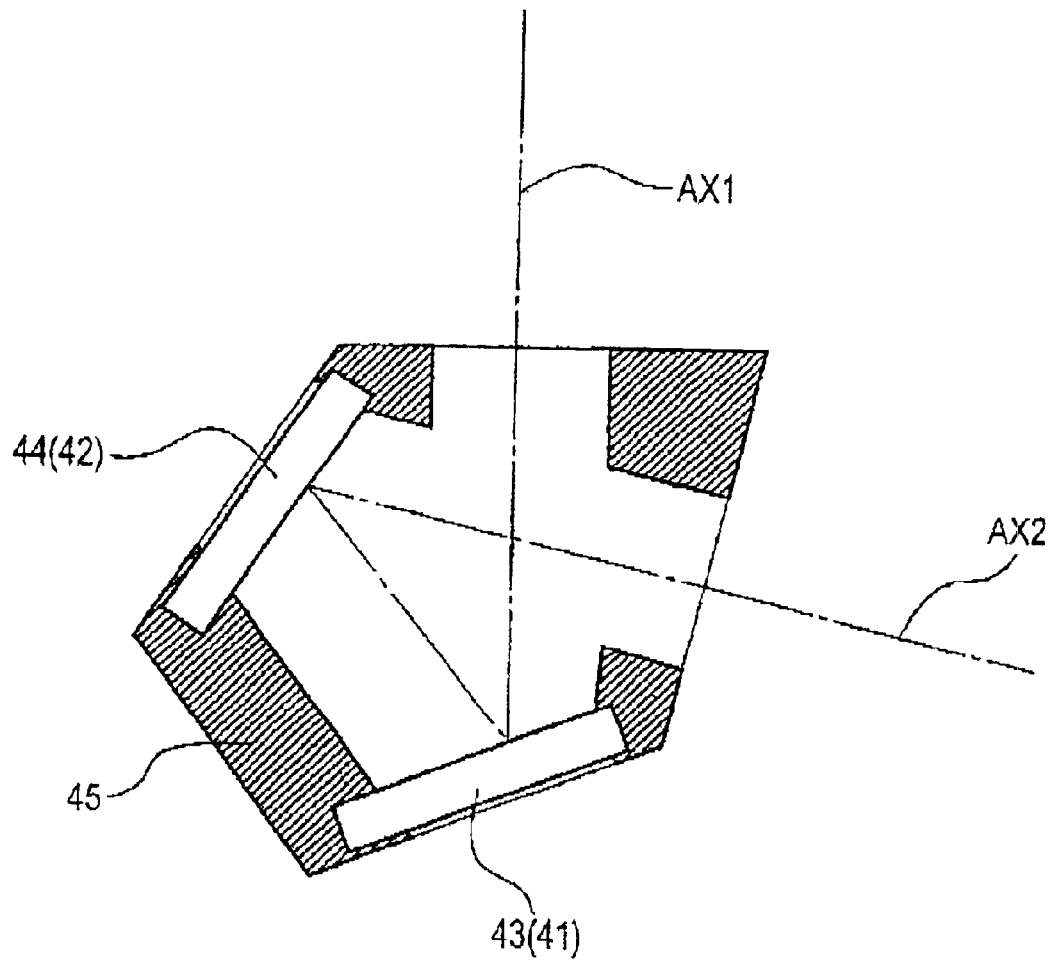
FIG. 8 schematically illustrates the structure of a variation of light beam detector.

While the light beam deflector are constituted of pentaprisms in the embodiment shown in FIG. 1, the light beam deflector may be instead constituted by using a pair of reflecting mirrors that are not parallel to each other and holding members that interlock and hold the pair of reflecting mirrors by interfitting with them. FIG. 8 schematically illustrates a structure that may be adopted in such a variation of the means for light flux deflection and FIG. 9 schematically illustrates the structure of the holding members in FIG. 8.

In the variation shown in FIG. 8, a first reflecting mirror 41 and a second reflecting mirror 42 respectively having reflection surfaces corresponding to the first reflection surface and the second reflection surface of the pentaprism 6 in FIG. 1 are interfitted with and held by a first mirror holding member 43 and a second mirror holding member 44 respectively. The first mirror holding member 43 and the second mirror holding member 44 are either formed as an integrated part of a base 45 or are mounted at the base 45. Thus, the base 45 holds the first reflecting mirror 41 and the second reflecting mirror 42 via the first mirror holding member 43 and the second mirror holding member 44 so as to sustain the angle of intersection $\Psi$ formed by the reflection surface of the first reflecting mirror 41 and the reflection surface of the second reflecting mirror 42 unchanged.

Figure 9A:
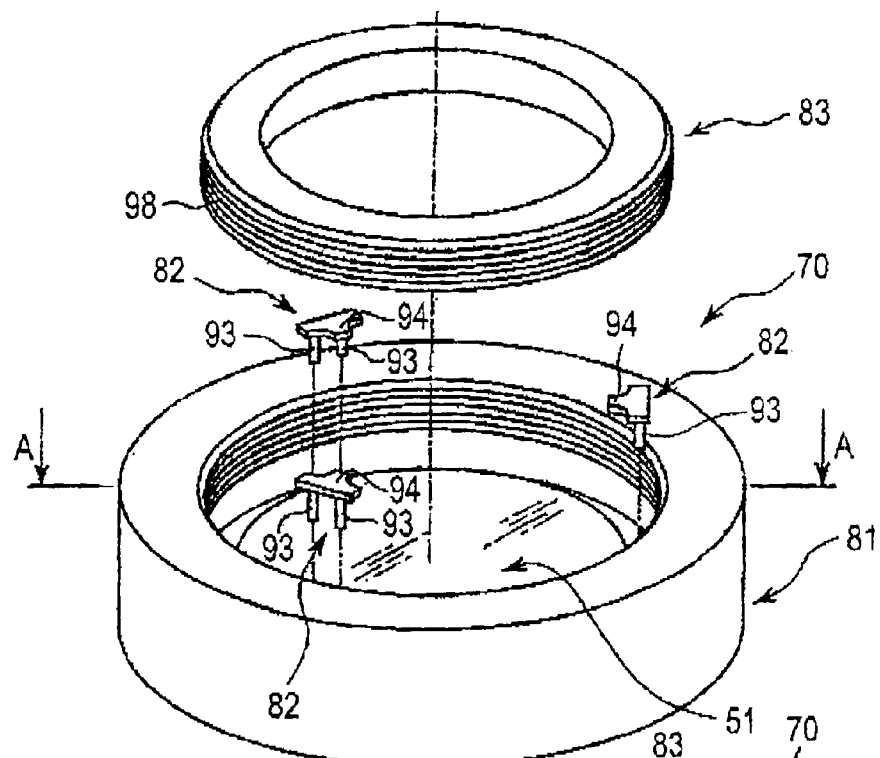
FIGS. 9($a$), 9($b$), 9($c$) schematically illustrate the structure of the holding members in FIG. 8.
Figure 9B:
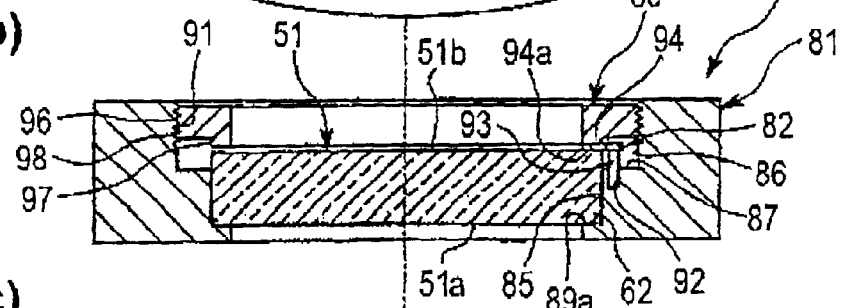
Figure 9C:
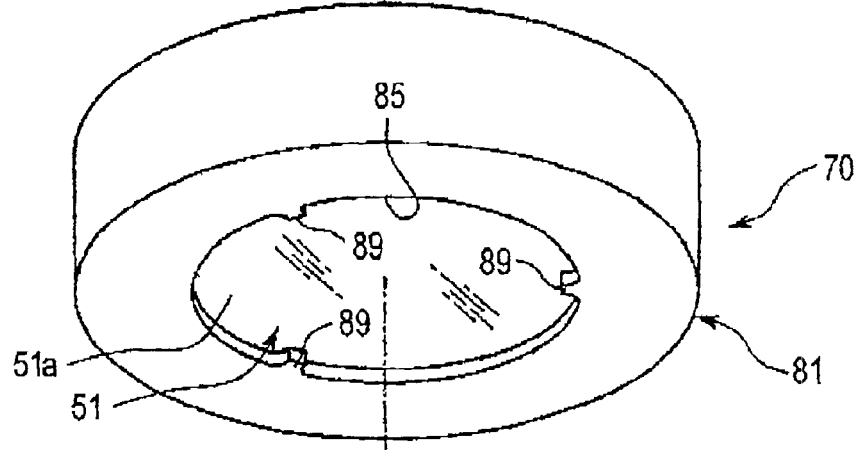

In FIG. 9, a mirror holding member 70 (which corresponds to the first mirror holding member 43 and the second mirror holding member 44 in FIG. 8) holds a reflecting mirror 51, which corresponds to the first reflecting mirror 41 and the second reflecting mirror 42 in FIG. 8 achieving rotation symmetry (having a disk shape with a constant thickness and a constant external diameter, more specifically) and is provided with an optical element holding metal member 81, spacers 82 and a retainer ring 83.

The optical material holding metal hardware piece 81, assumes a staged shape on its internal circumferential side and assumes a roughly cylindrical shape with a constant diameter on its external circumferential side. That is, at on internal circumference, a first internal diameter portion 85 is formed on one side along the direction in which the axis extends and a second internal diameter portion 86 is formed on the other side along the axial direction. The first internal diameter portion 85 has a diameter smaller than that of the second internal diameter portion 86 and, as a result, a step 87 is formed perpendicular to the direction in which the axis extends.

Three trapezoidal support portions 89 are formed so as to project outward toward the center at the end of the first internal diameter portion 85 on the side opposite from the side where the second internal diameter portion 86 is formed. These support portions 89 are formed in identical shapes, and are provided over equal intervals along the circumferential direction at the optical element holding metal member 81. The support portions 89 are each provided with a trapezoidal contact surface 89a perpendicular to the direction along which the axis extends, toward the second internal diameter portion 86 along the direction of the axis of the optical element holding metal member 81. These contact surfaces 89a, which have identical shapes, are set within a single plane perpendicular to the direction of the axis of the optical element holding metal member 81.

In addition, a female screw 91 is formed at the end of the second internal diameter portion 86 on the side opposite from the side where the first internal diameter portion 85 is provided. At the stair-like portion 87, insertion holes (only one is shown) 92 each paired and aligned with the support portion 89 along the radial direction are formed. The reflecting mirror 51 is inserted through the second internal diameter portion 85 to the optical element holding metal member 81 so that a peripheral portion 62 at the other surface 51a of the reflecting mirror 51 is mounted at the contact surfaces 89a of the support portions 89. The spacers 82 are each mounted at the corresponding insertion hole 92, and are each provided with a pair of parallel shafts 93 inserted at the insertion hole 92 and a mounting plate 94 extending from the shafts 93 along a direction perpendicular to the axial direction. By inserting the individual spacers 82 at the insertion holes 92, a contact surface 94a of the mounting plate 94 of each spacer 82 is placed in contact with the peripheral portion 62 at a surface 51b of the reflecting mirror 51.

The shape of the contact surfaces 94a of the mounting plates 94 placed in contact with the surface 51b of the reflecting mirror 51 matches the shape of the contact surfaces 89a of the support portions 89 placed in contact with the other surface 51a of the reflecting mirror 51. As a result, these contact surfaces 94a and 89a have areas equal to each other. In addition, the corresponding contact surfaces 94a and 89a are set at positions facing opposite each other (at matching positions along the direction of the circumference of the optical material holding metal hardware piece 81).

The retainer ring 83 assumes a stair-like shape on its external circumferential side and a roughly ring shape with a constant diameter on its internal circumferential side. That is, on its external circumferential side, a first external diameter portion 96 is formed on one side along the axial direction and a second external diameter portion 97 is formed on the other side along the axial direction. The first external diameter portion 96 has a diameter larger than the diameter of the second external diameter portion 97, with a male screw 98 formed at the first external diameter portion 96. The retainer ring 83 is mounted at the metal member 81 by interlocking the male screw 98 with the female screw 91 of the optical element holding metal member 81 having the reflecting mirror 51 inserted at the first internal diameter portion 85 and all the spacers 82 mounted therein. When the retainer ring 83 is screwed in at the optical element holding metal member 81, the reflecting mirror 51 is clamped by the trapezoidal contact surfaces 89a of the support portions 89 and the trapezoidal contact surfaces 94a of the mounting plates 94 from the two sides along the axial direction.

By utilizing the mirror holding member 70, it is possible to hold the reflecting mirror 51 without having to use an adhesive. As a result, the reflection surface of the reflecting mirror 51 is effectively prevented from becoming tilted within the plane of incidence as a result of deformation or the like of the adhesive attributable to, for instance, ambient air temperature fluctuations. It is to be noted that it is desirable to constitute the pair of mirror holding members 43 and 44 and the base 45 with a material having a coefficient of thermal expansion equal to or lower than 1 ppm/K, which does not expand readily when heated, to sustain the angle of intersection of the pair of reflecting mirrors 41 and 42 unchanged. More specifically, these members may be formed by using a low thermal expansion ceramics, a low thermal expansion glass, alloy or the like.

It is to be noted that while the pentaprisms 6 and 7 are provided respectively in the optical path between the projection optical system (4, 5) and the detection target surface Wa and the optical path between the condenser optical system (8, 9) and the detection target surface Wa in the embodiment and its variation described above, the advantages of the present invention may be achieved by providing a pentaprism in, at least, either of the optical paths.

In addition, while an explanation is given above in reference to the embodiment and the variation on an example in which a projection exposure apparatus is provided with a single surface position detection device, the present invention is not restricted by these details, and a plurality of surface position detection devices may be provided as necessary to perform detection over individual areas achieved by partitioning the detection field. In such a case, the individual devices can be calibrated based upon the results of detection obtained at a common field contained in both the detection field in which the detection is performed by a first surface position detection device and the detection field in which the detection is performed by a second surface position detection device.

While a light beam deflector is constituted by using a pentagonal prism having a pair of reflection surfaces or a mirror assembly having a pair of reflecting mirrors in the embodiment and the variations explained above, the present invention is not limited to these particulars, and a light beam deflector may be constituted by using a prism having an even number of reflection surfaces or a mirror assembly having an even number of reflection surfaces.

Furthermore, while the present invention is adopted in detection of the surface position of a photosensitive substrate in a projection exposure apparatus in the embodiment and the variations, it may also be adopted in detection of the surface position of a mask in a projection exposure apparatus.

Also, while the present invention is adopted in detection of the surface position of a photosensitive substrate in a projection exposure apparatus in the embodiment and the variations, it may also be adopted in detection of the surface position of an ordinary detection target surface, instead.

As explained above, in the surface position detection device according to the present embodiments, which is provided with light beam deflector each constituted of, for instance, a pentaprism, in the optical path between the projection optical system and the detection target surface and the optical path between the condenser optical system and the detection target surface to greatly deflect the optical path of the light beam entering the detection target surface and the optical path of a light beam having been reflected at the detection target surface, the projection optical system and the condenser optical system are allowed to be set over distances from the detection target surface to free these optical systems from any structural and positional restrictions imposed by the proximity of the detection target surface.

In addition, even when the pentaprism becomes tilted by a slight degree within, for instance, the plane of incidence as a result of displacement or deformation of the holding member attributable to vibration from the outside, temperature fluctuations and the like, the angle of deflection achieved at the pentaprism remains unchanged, i.e., the exiting light beam advances along a constant direction and, ultimately, that angle of incidence of the light beam entering the detection target surface or the light-receiving surface, too, remains unchanged. As a result, since hardly any changes occur in the angles of incidence at the detection target surface and the light-receiving surface and the entry positions at the detection target surface and the light-receiving surface, occurrence of a detection error attributable to external vibration, temperature fluctuations and the like can be successfully prevented.

Moreover, by adopting the surface position detection device according to the present invention in detection of the surface position of a photosensitive substrate relative to the projection optical system in a projection exposure apparatus, highly accurate alignment of the mask pattern surface and the exposure target surface of the photosensitive substrate relative to the projection optical system is achieved essentially without being affected by vibration of the projection exposure apparatus, ambient air temperature fluctuations or the like and, as a result, appropriate micro devices can be manufactured.

What is claimed is:

1. A surface position detection device for detecting a surface position of a detection target surface comprising;
   a projection system, optically connected to the detection target surface, for protecting a light beam along an oblique direction onto the detection target surface;
   a light-receiving system, optically connected to the detection target surface, for receiving a light beam reflected by the detection target surface;
   a light beam deflector, provided, at least, either in an optical path of the projection optical system or in an optical path of the light-receiving system, having an even number of reflection surfaces to allow an incident light beam to exit at an angle that is not parallel to an entry angle of the incident light beam,
   wherein the surface position of the detection target surface is detected based upon an output from the light-receiving system.

2. The surface position detection device of claim 1, wherein the light beam deflector includes a prism having a pairing of reflection surfaces that are not parallel to each other.

3. The surface position detection device of claim 2, wherein the prism includes:
   a first transmission surface through which the incident light beam is transmitted;
   a first reflection surface at which the light beam; having been transmitted through the first transmission surface and propagated through an inside of the prism, is reflected;
   a second reflection surface, at which the light beam having been reflected at the first reflection surface and propagated through the inside of the prism, is reflected along an optical path intersecting an optical path of the light beam having been transmitted through the first transmission surface;
   and a second transmission surface through which the light beam, having been reflected at the second reflection surface and propagated through the inside of the prism, is transmitted.

4. The surface position detection device of claim 3, wherein an angle formed by the first and second reflection surfaces is set within a range of 40° or more and less than 45°.

5. The surface position detection device of claim 4, wherein the prism comprises a low-dispersion optical material with an Abbe number of 65 or higher.

6. The surface position detection device of claim 4, wherein the prism comprises a low thermal expansion optical material with a thermal expansion coefficient equal to or lower than 1 ppm/k.

7. The surface position detection device of claim 2, wherein the prism comprises a low-dispersion optical material with an Abbe number of 65 or higher.

8. The surface position detection device of claim 2, wherein the prism comprises a low thermal expansion optical material with a thermal expansion coefficient equal to or lower than 1 ppm/K.

9. The surface position detection device of claim 1, wherein the light beam deflector includes a pair of reflection mirrors, and a holding member mechanically connected to the pair of reflection mirrors.

10. The surface position detection device of claim 9, wherein the pair of reflection mirrors reflect the incident light beam along an optical path intersecting an optical path of the incident light beam.

11. The surface position detection device of claim 10, wherein the holding member comprises a low thermal expansion with a thermal expansion coefficient equal to or lower than 1 ppm/K.

12. The surface position detection device of claim 9, wherein the holding member comprises a low thermal expansion material with a thermal expansion coefficient equal to or lower than 1 ppm/K.

13. The surface position detection device of claim 1, wherein the reflection surfaces of the light beam deflector reflect the incident light beam along an optical path intersecting an optical path of the incident light beam.

14. The surface position detection device of claim 1, wherein the even number of reflection surfaces are arranged in at least one of an optical path between a the detection target surface and a side lens surface of the projection system and an optical path between the detection target surface and a side lens surface of the light-receiving system.

15. The surface position detection device of claim 14, wherein the projection system and the light-receiving system has detection target side telecentricity.

16. The surface position detection device of claim 15, wherein the projection system projects an image of a pattern onto the detection target surface.

17. An exposure apparatus for exposing a pattern onto a photosensitive substrate, comprising:
   a surface position detection device for detecting a surface position of the photosensitive substrate, comprising:
   a projection system, optically connected to the photosensitive substrate, for protecting a light beam along an oblique direction onto the photosensitive substrate,
   a light-receiving system, optically connected to the photosensitive substrate, for receiving a light beam reflected by the photosensitive substrate;
   a light beam deflector, provided, at least, either in an optical path of the projection optical system or in an optical path of the light-receiving system, having an even number of reflection surfaces to allow an incident light beam to exit at an angle that is not parallel to an entry angle of the incident light beam,
   wherein the surface position of the photosensitive substrate is detected based upon an output from the light-receiving system;
   a surface holder; and
   a controller,
   wherein the controller controls a position of the substrate holder based upon an output from the surface position device.

18. A method for exposing a pattern onto a substrate, comprising:
   detecting a position of the substrate with a surface position detection device that includes:
   a projection system, optically connected to substrate, for projecting a light beam along an oblique direction onto the substrate;
   a light-receiving system, optically connected to the substrate, for receiving a light beam reflected by the substrate;
   a light beam deflector, provided, at least, either in an optical path of the projection optical system or in an optical path of the light-receiving system, having an even number of reflection surfaces to allow an incident light beam to exit at an angle that is not parallel to an entry angle of the incident light beam, wherein the position of the substrate is detected based upon an output from the light-receiving system;

controlling the position of the substrate based upon an output from the surface position detection device; and exposing the pattern onto the substrate.

19. A method for detecting a surface position of a detection target comprising:

projecting a light beam along an oblique direction onto the detection target surface;

receiving a light beam reflected by the detection target surface;

deflecting at least either one of an optical path of the protected light beam or an optical path of the received light beam with an even number of reflection surfaces to allow an incident light beam to exit at an angle that is not parallel to an entry angle of the incident right beam; and detecting the surface position of the detection target based upon the received light beam.

20. The method of claim 19, wherein the reflection surfaces reflect the incident light beam along an optical path intersecting an optical path of the incident light beam.

21. The method of claim 20, wherein the reflection surfaces are formed on a prism.

22. The method of claim 21, wherein the prism comprises a low-dispersion optical material with an Abbe number of 65 or higher.

23. The method of claim 22, wherein at least one of the step of projecting the light beam and the step of receiving the light beam comprises a step of oscillating the light beam.

24. The method of claim 21, wherein the prism comprises a low thermal expansion material with a thermal expansion coefficient equal to or lower than 1 ppm/K.

25. The method of claim 20, wherein the reflection surfaces are formed on surfaces of mirrors which are held by a holding member.

26. The method of claim 25, wherein the holding member comprises a low thermal expansion material with a thermal expansion coefficient equal to or lower than 1 ppm/K.

27. The method of claim 20, wherein an angle formed by the reflection surfaces is set within a range of 40° or more and less than 45°.

28. The method of claim 19, wherein the step of deflecting the optical path is performed between the step of projecting the light beam and the step of receiving the light beam.

29. The method of claim 28, wherein the step of projecting the light beam comprises a step of projecting an image of a pattern onto the detection target surface.

30. A method of exposing a pattern onto a substrate, comprising:

projecting a light beam along an oblique direction onto the substrate;

receiving a light beam reflected by the substrate;

deflecting at least either one of an optical path of the projected light beam or an optical path of the received light beam with an even number of reflection surfaces to allow an incident light beam to exit at an angle that is not parallel to an entry angle of the incident light beam; and detecting the surface position of the substrate based upon the received light beam;

controlling the position of the substrate based upon an output from the detecting device; and exposing the pattern onto the substrate.

31. A surface position detection device for detecting a surface position of a detection target surface, comprising:

a projection system, optically connected to the detection target surface, for projecting a light beam along an oblique direction onto the detection target surface;

a light-receiving system, optically connected to the detection target surface, for receiving a light beam reflected by the detection target surface;

a light beam deflector, provided, at least, either in an optical path of the projection optical system or in an optical light-receiving system, having an even number of reflection surfaces to allow an incident light beam to exit at an angle that is not parallel to an entry angle of the incident light beam, wherein:

the surface position of the detection target surface is detected based upon an output from the light-receiving system.

the light beam deflector includes a prism having a pairing of reflection surfaces that are not parallel to each other, the prism includes:

a first transmission surface through which the incident light beam is transmitted;

a first reflection surface at which the light beam; having been transmitted through the first transmission surface and propagated through an inside of the prism, is reflected;

a second reflection surface, at which the light beam having been reflected at the first reflection surface and, propagated through the inside of the prism, is reflected along an optical path intersecting an optical path of the light beam having been transmitted through the first transmission surface;

and a second transmission surface through which the light beam, having been reflected at the second reflection surface and propagated through the inside of the prism, is transmitted.

an angle formed by the first and second reflection surfaces is set within a range of 40° or more and less than 45°.

the prism comprises a low-dispersion optical material with an Abbe number of 65 or higher, and the projection system comprises an oscillating mirror arranged in the optical path of the projection system or in the optical path of the light-receiving system.

32. An exposure apparatus for exposing a pattern onto a photosensitive substrate, the exposure apparatus comprising:

a surface position detection device for detecting a surface position of the photosensitive substrate, including:

a projection system, optically connected to the photosensitive substrate, for projecting a light beam along an oblique direction onto the photosensitive substrate;

a light-receiving system, optically connected to the photosensitive substrate, for receiving a light beam reflected by the photosensitive substrate;

a light beam deflector, provided, at least, either in an optical path of the projection optical system or in an optical path of light-receiving system, having an even number of reflection surfaces to allow an incident light beam to exit at an angle that is not parallel to an entry angle of the incident light beam, wherein the surface position of the photosensitive substrate is detected based upon an output from the light-receiving system, the even number of reflection surfaces are arranged in at least one of an optical path between a the detection target surface and a side lens surface of the projection system and an optical path between the detection target surface and a side lens surface of the light-receiving system, and the projection system and the light-receiving system has detection target side telecentricity;

a substrate holder; and a controller, wherein the controller controls a position of the substrate holder based upon an output from the surface position detection device.

33. A method for exposing a pattern onto a substrate, comprising:

detecting a position of the substrate with a surface position detection device that includes:

a projection system, optically connected to the substrate, for projecting a light beam along an oblique direction onto the substrate;

a light receiving system, optically connected to the substrate, for receiving a light beam reflecting by the substrate, a light beam deflector, provided, at least, either in an optical path of the projection optical system or in an optical path of the light-receiving system, having an even number of reflection surfaces to allow an incident light beam to exit at an angle that is not parallel to an entry angle of the incident light beam, wherein the surface position of the substrate is detected based upon an out from the light-receiving system, the even number of reflection surfaces are arranged in at least one of an optical path between a the detection target surface and a side lens surface of the projection system and an optical path between the detection target surface and a side lens surface of the light-receiving system, and the projection system and the light-receiving system has detection target side telecentricity;

controlling the position of the substrate based upon an output from the surface position detection device; and exposing the pattern onto the substrate.

* * * * *

UNITED STATES PATENT AND TRADEMARK OFFICE
CERTIFICATE OF CORRECTION

PATENT NO. : 6,897,462 B2
DATED : May 24, 2005
INVENTOR(S) : Toru Kawaguchi

It is certified that error appears in the above-identified patent and that said Letters Patent is hereby corrected as shown below:

Column 21,
Line 8, "comprising;" should read -- comprising: --.
Line 32, "beam; having" should read -- beam having --.
Line 56, "ppm/k." should read -- ppm/K. --.

Column 22,
Line 19, "between a the detection" should read -- between a detection --.
Line 25, "has" should read -- have --.
Line 35, "protecting" should read -- projecting --.
Line 36, "substrate," should read -- substrate; --.

Column 23,
Line 17, "protected" should read -- projected --.
Line 21, "right" should read -- light --.

Column 24,
Line 23, "system." should read -- system, --.
Line 30, "beam;" should read -- beam --.
Line 37, "and, propagated" should read -- and propagated --.
Line 44, "transmitted." should read -- transmitted, --.
Line 47, "45°." should read -- 45°, --.
Line 67, "of light-receiving" should read -- of the light-receiving --.

Column 25,
Line 8, "between a the detection" should read -- between a detection --.
Line 12, "has" should read -- have --.

UNITED STATES PATENT AND TRADEMARK OFFICE
CERTIFICATE OF CORRECTION

PATENT NO. : 6,897,462 B2
DATED : May 24, 2005
INVENTOR(S) : Toru Kawaguchi

It is certified that error appears in the above-identified patent and that said Letters Patent is hereby corrected as shown below:

<u>Column 26,</u>
Line 1, "light receiving" should read -- light-receiving --.
Line 2, "reflecting" should read -- reflected --.
Line 3, "substrate," should read -- substrate; --.
Line 11, "out" should read -- output --.
Lines 13-14, "between a the detection" should read -- between a detection --.
Line 18, "has" should read -- have --.

Signed and Sealed this

Twenty-seventh Day of September, 2005

JON W. DUDAS
*Director of the United States Patent and Trademark Office*